United States Patent [19]

Buck

[11] Patent Number: 4,512,340

[45] Date of Patent: Apr. 23, 1985

[54] VISIBLE LIGHT CURED ORTHOPEDIC POLYMER CASTS

[75] Inventor: Carl J. Buck, Berkeley Heights, N.J.

[73] Assignee: Johnson & Johnson Products, Inc., New Brunswick, N.J.

[21] Appl. No.: 468,434

[22] Filed: Feb. 22, 1983

[51] Int. Cl.$^3$ .............................................. A61F 13/04
[52] U.S. Cl. .................................. 128/90; 204/159.15
[58] Field of Search .................... 128/90, 89; 528/359; 525/186, 189, 354; 204/159.14, 159.15, 159.19, 159.23, 159.24

[56] References Cited

U.S. PATENT DOCUMENTS

| | | | |
|---|---|---|---|
| 3,421,501 | 1/1969 | Beightol | 128/90 |
| 3,613,675 | 5/1969 | Larsen | 128/90 |
| 3,874,376 | 4/1975 | Dart et al. | 128/90 |
| 3,881,473 | 5/1975 | Corvi et al. | 128/90 |
| 3,905,376 | 9/1975 | Johnson et al. | 128/595 |
| 4,071,424 | 1/1978 | Dart et al. | 204/159.15 |
| 4,235,686 | 11/1980 | Dart et al. | 204/159.19 |

FOREIGN PATENT DOCUMENTS 1512553 6/1978 United Kingdom .

OTHER PUBLICATIONS

Encyclopedia of Chemical Technology, vol. 23, pp. 577-592, "Curing by U.V. Radiation", (Part 2), J. Ohngemach, et al., Kontakte 3,15, (1980).

*Primary Examiner*—John D. Yasko
*Attorney, Agent, or Firm*—Leonard Kean

[57] ABSTRACT

An orthopedic cast material is disclosed, which, when wrapped about a body member and cured by exposure to visible light, forms a rigid, high strength immobilizing structure and which comprises an air, light and X-ray permeable fabric impregnated with a formulation comprising (a) acrylate terminated polyurethane oligomers or ethylenically unsaturated polyesters or polyethers, (b) functional acrylate monomers as optional diluents and (c) a photoinitiator which is activated by visible light to initiate the polymerization reaction, whereby the casts produced therefrom show no tendency towards discoloration in ambient light or sunlight, are aesthetic in appearance, are dry to the touch and possess good whiteness.

33 Claims, No Drawings

VISIBLE LIGHT CURED ORTHOPEDIC POLYMER CASTS

BACKGROUND OF THE INVENTION

This invention relates to an orthopedic cast material which, when wrapped about a body member and cured by exposure to visible light, forms a rigid, high strength immobilizing structure and which comprises an air, light and X-ray permeable fabric impregnated with a formulation comprising: (a) acrylate terminated polyurethane oligomers, (b) functional acrylate diluent monomers as optional ingredients and (c) a photoinitiator which is activated by visible light to initiate the polymerization reaction, whereby the casts produced therefrom show no tendency towards discoloration in ambient light or sunlight. This invention also relates to the formulation used for preparing the cast material, and the method of forming the cast as well as the cast itself.

Previously, a leg, arm or finger was immobilized by applying a Plaster-of-Paris bandage which subsequently dried to form an immobilizing orthopedic cast. Such bandages suffer from the disadvantage that the resultant casts are heavy, uncomfortable to wear, insufficiently permeable to air and, once set, they rapidly lose their strength when brought into contact with water. Furthermore, such casts are generally impermeable to X-rays so that if the body member is to be examined by X-rays the cast must first be removed from the body member. In such cases, when the cast has been removed it may be found that the body member has not healed sufficiently and it may then be necessary to reapply a bandage to the body member and reform a cast. This is obviously inconvenient.

Many attempts have been made to provide bandaging materials which are free from the above disadvantages. It has, for example, been attempted to impregnate bandaging material with polymer solutions which harden under exposure to ultraviolet light. The ultraviolet lamps required for this purpose are difficult to handle and, moreover, the ultraviolet light only reaches the upper layers of the bandage so that the deeper layers harden only after a considerable time, if at all. The use of ultraviolet radiation suffers from the further disadvantage that it is known to be harmful to the human eye and skin (e.g. burns) and when using ultraviolet radiation it may be necessary to take considerable care to shield the patient and the operator from the radiation during formation of the cast.

In order to overcome the above-mentioned disadvantages, it has been proposed to use orthopedic casting bandages produced from polyurethane prepolymers and which are hardened, or cured, by exposure to visible light radiation. To circumvent the need for ultraviolet light curing, a number of moisture-cured polymer cast systems based on isocyanate-terminated urethane prepolymer compositions have been marketed. The polyurethane casting bandages suffer from some of the same disadvantages as the Plaster-of-Paris bandages. The curing of these cast bandages is initiated by immersion into water and afford lightweight, X-ray transparent, porous (breathable) polymer casts which cure sufficiently within fifteen to thirty minutes to a weight-bearing strength. While superior to Plaster-of-Paris in ease of application to body members, rapid setting characteristics, and permeability to X-rays, the polyurethane based bandages suffer from some disadvantages. For example, the polymerizable polyurethane prepolymer formulation contains a polymerization catalyst which is, in part, responsible for the reduced thermal stability of the casting bandages during prolonged storage, where the bandage may undergo premature polymerization and hardening prior to removal from the package.

Premature polymerization of the isocyanate-terminated urethane prepolymer can occur also if traces of moisture enter the package during storage. Accordingly, it is absolutely necessary that such prepolymer be prepared, coated onto bandage strips, and packaged in sealed containers under strictly anhydrous, or nearly so, conditions if one is to preclude hardening of the casting tape during storage and prior to actual use. Furthermore, it has been found that the cured urethane prepolymer based orthopedic casts are sensitive to discoloration (yellowing) on exposure to ambient visible light and, in particular, to ultraviolet radiation (sunlight).

By using visible light to effect the cure of the organic material to produce the immobilizing cast, it is unnecessary to protect the patient and operator from the source of light as would be the case wherein the organic material is cured by exposure to ultraviolet radiation. Consequently, the use of visible light is more convenient, particularly for the operator. Furthermore, the orthopedic cast produced from the impregnated fabric of the invention is lightweight and thus is convenient to wear and is permeable to X-rays. Visible light sources are, of course, relatively cheap and are readily available as contrasted with ultraviolet radiation sources.

The use of a visible light source to effect photocuring of ethylenically unsaturated resin compositions is disclosed in U.S. Pat. Nos. 3,874,376; 4,071,424 and 4,235,686. U.S. Pat. No. 3,874,376 relates to visible light photocurable resin impregnated fabrics for use in preparing orthopedic immobilization devices. A method is disclosed for producing rigid orthopedic casts by means of exposure to visible light (400–750 nm wavelength range) of fabrics of various types which are impregnated with compositions consisting of ethylenically-unsaturated resins and monomers, a photosensitizer activatable by visible light and certain photopolymerization accelerators. Although this patent broadly discloses photopolymerizable formulations and refers to a composition containing at least one photosensitizer activatable by visible light in the 400–750 nm wavelength range, actual photosensitizers disclosed are the diketone type, in particular, benzil, camphorquinone, α-naphthil and p-tolil. Other specific photosensitizers disclosed are fluorenone, uranyl salts of various types, combinations of manganese carbonyl and organic halides and a number of photosensitive dyes which absorb actinic radiation in the visible light wavelength range. The preferred photosensitizers of U.S. Pat. No. 3,874,376 are fluorenone or the α-diketones. However, the benzil, camphorquinone and fluorenone photoinitiators tend to impart an unaesthetic yellow coloration to the cast when used at concentrations required to give rapid visible light cures. U.S. Pat. Nos. 4,071,424 and 4,235,686 merely relate to different aspects of the invention disclosed in U.S. Pat. No. 3,874,376.

U.S. Pat. No. 3,613,675 discloses ultraviolet light photocurable resin impregnated bandages for orthopedic cast applications. The resins used are blends of ethylenically or acetylenically-unsaturated monomers and polymers with various polythiols, catalyzed with photoinitiators such as the benzophenones, acetophenone and methyl ethyl ketone. Curing is effected by means of exposure to sunlamps, sunlight or radiation from xenon lamps, thereby requiring protection of the skin of the patient from burn damage. Furthermore, the use of the photoinitiators of U.S. Pat. No. 3,613,675 tends to result in nonaesthetic, discolored polymer casts.

Ultraviolet curable orthopedic cast materials, impregnated with a photosensitizer and photocurable (meth)acrylate terminated urethane prepolymers containing at least two reactive carbon-carbon double bonds, are also disclosed in British Pat. No. 1,512,553. The compositions of the latter patent are cured rapidly by photoinitiated polymerization and crosslinking of the two or more (meth)acrylate groups and do not require use of volatile and odoriferous crosslinking comonomers, such as disclosed in U.S. Pat. No. 3,421,501 and 3,881,473. However, the major disadvantage of this polymer cast system is the use of ultraviolet light and the hazards associated therewith.

In view of the fact that the catalysts used in accordance with the prior art (such as those disclosed in U.S. Pat. No. 3,874,376) result in non-aesthetic polymer casts, it is indeed surprising that the catalysts utilized in accordance with the present invention bring about a cast which is essentially white in color and which does not yellow when exposed to ambient light or to sunlight. Furthermore, the method of the closest prior art (as exemplified by U.S. Pat. No. 3,874,376) requires the use of a reducing agent which is normally an amine, as well as a photosensitive catalyst. In accordance with the present invention, on the other hand, such reducing agent is not essential. In fact, Applicant has found that when amines are added, the depth of cure of the cast may not be as good and the surface of the cast may tend to be somewhat tacky. In accordance with one aspect of the present invention, Applicant has found that the addition of certain polyfunctional mercaptans, which participate in the reaction, result in dry surface cures.

SUMMARY OF THE INVENTION

The present invention relates to an orthopedic cast material which, when wrapped about a body member and cured by exposure to visible light, forms a rigid, high strength immobilizing structure and which comprises an air, light and X-ray permeable fabric impregnated with a formulation comprising (a) one or more acrylate terminated polyurethane oligomers or ethylenically-unsaturated polyesters or polyethers, (b) optionally, one or more functional acrylate or methacrylate monomers as reactive diluents and (c) a photoinitiator which is activated by visible light in the wavelength range 400 nm to 750 nm to generate free radicals to initiate the photopolymerization reaction, said photoinitiator being selected from the group consisting of (A) 1-hydroxy-1-cyclohexyl phenyl ketone of the formula

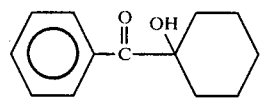

(B) (ring substituted or unsubstituted) 2-hydroxy 2,2-dimethyl acetophenone of the formula

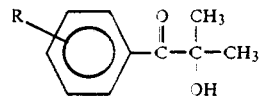

wherein the substituents R are selected from the group consisting of hydrogen, methyl, dimethyl, isopropyl, tertbutyl, chloro, bromo and fluoro, or (C) blends of (A) or (B) with azobis (isobutyronitrile) of the formula

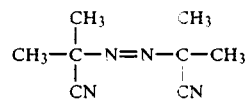

whereby the casts produced therefrom show no tendency towards discoloration in ambient light or sunlight.

It is preferred that the formulation also include a surface cure modifier so that after curing the resultant cast is non-tacky. The surface cure modifiers utilized in accordance with the invention are preferably esters of 3-mercapto propionic acid, such as trimethylolpropane tris(3-mercaptopropionate), pentaerythritol tetrakis (3-mercaptopropionate) and polyethylene glycol di(3-mercaptopropionate).

It is desirable that the formulation should include fillers or other opacifying agents to improve cast whiteness and optionally other additives to modify the flow characteristics of the formulation and improve the dark storage stability.

The preferred fabric consists of a fiberglass web, the formulation comprising between 40% and 60% by weight of the total weight of the impregnated material.

In the formulation of the invention, it is preferred that the photoinitiators or blends of two or more photoinitiators comprise from about 0.5% to about 20% by weight (and more preferably from about 5% to 15% by weight) based on the total weight of the (meth) acrylate monomer components.

In the formulation of the invention, it is preferred that the weight ratio of the oligomers (a) to the reactive diluent monomers (b) should vary between 40/60 and 100/0. The weight ratio of (a) to (b) may also desirably vary between 60/40 and 80/20.

A preferred formulation of the invention comprises about 70 parts of oligomer (a), about 30 parts of reactive diluent monomer (b), about 10 parts of a photoinitiator (c), about ten parts of a surface cure modifier, and between 0 and 5 parts of an opacifying agent.

In the material of the invention the following components are preferred:

(a) is an aliphatic type diacrylate-terminated polyurethane oligomer;

(b) is trimethylolpropane triacrylate or pentaerythritol triacrylate;

(c) is a photoinitiator of structure (A) or (B) and the surface cure modifier is trimethylolpropane tris(3-mercaptopropionate) and the opacifying agent is zinc diacrylate, and the fabric comprising a fiberglass web.

In a further desirable embodiment of the invention, the components of the formulation are present in the following weight ratios:

About 100 parts of oligomer (a), 0 parts of monomer (b), 10 parts of the photoinitiator (c), 0 to 10 parts of trimethylolpropane tris(3-mercaptopropionate) as a surface cure modifier (d), and 0 to 5 parts of zinc diacrylate as an opacifying agent (e).

In one desirable formulation of the invention, the oligomeric monomer component (a) is prepared from isocyanate terminated prepolymers, wherein the isocyanate moiety and the prepolymer is either aliphatic or aromatic and the reactive diluent monomer (b) is a polyfunctional acrylate or methacrylate ester. A preferred filler in connection with said formulation is zinc diacrylate.

The present invention includes the package which is adapted to contain the impregnated fabric of the invention, which package comprises a light-proof aluminum foil sealed bag.

The present invention also includes the rigid, high strength immobilizing cast, which is porous, breathable and translucent, comprising the impregnated fabric which has been cured by exposure to light.

The invention also includes the formulation utilized for impregnating the fabric.

In addition, this invention includes the method of forming an orthopedic cast which comprises wrapping a body member with the material of the invention and curing and hardening the latter by exposing same to visible light in the wavelength range of 400 nm to 750 nm for at least two minutes.

DESCRIPTION OF THE PREFERRED EMBODIMENTS

In accordance with the present invention there is provided an orthopedic cast bandage suitable for application to a leg, arm, finger or other body member and from which an immobilizing orthopedic cast permeable to X-rays is obtained in which disadvantages of prior art orthopedic casts are substantially overcome. The present orthopedic cast bandage is stable and it avoids the use of heat, ultraviolet radiation or water activation to effect curing or hardening of the immobilizing orthopedic cast.

The present orthopedic cast bandage consists of a fiberglass fabric or other fabric material sufficiently transparent to visible light radiation, which is impregnated with a photopolymerizable monomer composition containing a photoinitiator activated by visible light. Upon exposure to visible light, photocuring is rapid and complete within about 10 minutes exposure to provide high strength, lightweight, non-tacky casts exhibiting the desired degree of whiteness and resistance to discoloration (yellowing) in ambient light or sunlight.

The photochemically sensitive binder coating on the casting bandages consists of an acrylate-terminated polyurethane oligomer, one or more polyfunctional acrylate or methacrylate monomers, a photoinitiator system, a surface cure modifier, and an opacifying agent (filler) to improve cast whiteness. Other additives such as antioxidants, light stabilizers and polymerization inhibitors (hindered phenols) may also be added to the formulation to improve the shelf-life stability of the impregnated bandage tape and minimize discoloration of the cast upon exposure to sunlight or ambient light.

Oxygen inhibition of polymerization is a common and undesirable side reaction which occurs during free radical polymerization of ethylenically-unsaturated monomers and can result in partially cured polymeric compositions having tacky surface properties. The specific photopolymerization monomer formulations used in the present invention are not as sensitive to oxygen-inhibition of polymerization, thereby providing aesthetic, hard, tack-free casts.

The sources of visible light used in this invention include those provided by incandescent spotlights of 150 watt capacity, tungsten-halogen lamps (Kodak Slide Projector), plant lights, daylight fluorescent tubes and other sources providing energy in the 400–750 nm wavelength range and essentially free of significant actinic radiation in the ultraviolet range (about 200 to 400 nm). In the practice of this invention for immobilization of cast-wrapped body members, a bank of such suitable light sources would be utilized to assure complete photocuring of the cast within a short time.

The rate of curing of the cast is dependent on the intensity of the visible light source. With the preferred tungsten/halogen and 150 watt spotlight sources, exposures at distances ranging from about 3 to 20 inches effected rapid photocuring of a 5-ply fiberglass casting bandage within ten minutes. The outermost surface layers of the cast generally cured to hard composites within about 1 to 2 minutes, with the balance of the ten-minute exposure period required to cure the deeper layers of the cast in contact with the body member.

As a result of the photosensitivity of the formulations to visible light, the fabrics are coated in subdued or diffuse lighting. To prevent premature photopolymerization and maintain good shelf storage stability, the impregnated fabrics are packed in light-proof aluminum foil sealed bags. Evaporation losses are insignificant because of the low volatility of the components of the photocurable formulations used in this invention. The shelf life of the casting tapes can be further improved by addition of certain free radical inhibitors (hydroquinone, p-methoxyphenol, 2,6-di-t-butyl-p-cresol, other hindered phenols) and ultraviolet absorbers to the monomer formulation, the concentrations being suitably adjusted so as to maintain a fast rate of photopolymerization when utilized as orthopedic immobilization casts or splints.

The methods for coating or impregnating the fiberglass casting bandages with the photopolymerizable monomer formulations can be varied. In one method, the fabric is dipped into the formulation and the impregnated bandages run through squeeze rolls to remove excess monomer. Higher viscosity formulations can be pre-warmed, if necessary, to improve their flow rate and facilitate even coating of the fabric bandages. Although less desirable from an environmental polution standpoint, the resin can be diluted to the desired applications viscosity with a volatile solvent, such as methylene chloride, toluene, and the like, and the bandage air dried in subdued lighting to obtain a substantially solvent-free resin impregnated casting bandage.

The primary monomer components of the photopolymerizable formulations are ethylenically-unsaturated polyesters, polyethers, and polyurethanes containing at least two acrylate or methacrylate groups capable of undergoing photoinitiated polymerization and cross-linking. The preferred monomers are the acrylate-terminated polyurethane oligomers of relatively high viscosity and available from several commercial sources. Examples are Uvithane 782, 783, 788, and 893M polyurethane oligomers sold by Thiokol Corporation; Uvimer 530 and 775 available from Polychrome Corp.; and Photomer 6008 from Diamond Shamrock Co.

The aliphatic type polyurethane oligomers (Uvithane 788 and 893, Uvimer 530, and Photomer 6008) are preferred over the corresponding aromatic types (Uvithane 782 and 783) due to greater resistance towards discoloration in sunlight or other ultraviolet light sources of the polymeric casts prepared therefrom.

Oligomeric acrylate and methacrylate terminated monomers, also suitable for visible light initiated photopolymerization, are those which can be readily prepared by esterification of polyol ethers, such as polyethylene glycol and poly(tetramethylene ether)glycol and hydroxyl-terminated polyesters, with (meth)acrylic acid. Direct esterification of carboxylic terminated polyesters with the hydroxyethyl and hydroxypropyl esters of (meth)acrylic acid provide reactive polymers as well. A specific example is the acrylate-epoxy resin, Epocryl 370, sold by Shell Chemical Co., and which has the following idealized structure:

Idealized Structure of Epocryl Resin 370

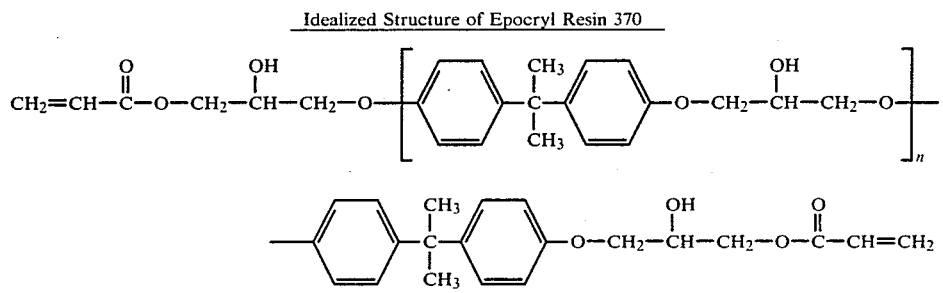

The (meth)acrylate oligomers mentioned above are generally high viscosity resins which can be somewhat difficult to formulate and apply to fabric bandages because of their viscosity. In order to overcome this problem, it is common practice to blend oligomeric monomers with lower viscosity polyfunctional acrylate and methacrylate monomers to achieve a more desirable applications viscosity. These polyfunctional monomers copolymerize with the oligomeric monomer components in the formulation and can often impart improved mechanical properties to the resultant photocured polymer. Typical polyfunctional monomers useful as reactive diluents are N-vinylpyrrolidone and the acrylate and methacrylate esters of ethylene glycol, diethylene glycol, triethylene glycol, tetraethylene glycol, 1,3-butylene glycol, 1,4-butanediol, 1,6-hexanediol, neopentyl glycol, trimethylolpropane, pentaerythritol, tripropylene glycol; tetrahydrofurfuryl alcohol, and ethylene glycol monomethyl ether. In accordance with the present invention the most preferred reactive diluents for the oligomeric (meth)acrylate monomers are 1,4-butanediol diacrylate, trimethylolpropane triacrylate, pentaerythritol triacrylate and tetraethylene glycol dimethacrylate. In general, the acrylate esters are preferred over the corresponding methacrylate esters because of their more rapid rate of photopolymerization and somewhat lesser sensitivity to oxygen-inhibition of polymerization at the polymer bandage/air interface.

The concentration of the oligomeric (meth)acrylate-terminated urethane and reactive diluent monomers can be varied so as to achieve a suitable applications viscosity, photopolymerization cure rate, and desirable strength properties of the cured polymer cast. The oligomeric monomer may be the sole monomer component in the photopolymerization formulation or it may be blended with the multifunctional (meth)acrylate monomers in different proportions. In the preferred composition of this invention, the monomer components may consist of about 40 to 100 parts by weight of one or more of the acrylate-terminated urethane oligomers and about 0 to 60 parts by weight of one or more of the reactive diluent monomers.

The photoinitiators are key ingredients in the photochemical formulation, since they function as the source of free radicals required for polymerization of the vinyl monomer components in the formulation. For the practice of this invention, only certain specific photoinitiators were found useful in providing aesthetic polymer casts which were not discolored after photocuring with visible light or following extended exposure of the polymer cast to ambient light or sunlight. Many of the photoinitiators commonly used in ultraviolet cured systems impart an undesirable yellow or other discoloration when utilized in the visible light cured formulations (such as those of the present invention), examples being photoinitiators such as benzil, camphorquinone, 9-fluorenone, 2-methylanthraquinone, diacetyl, benzanthrone, thioxanthen-9-one, and benzoin isobutyl ether. A number of these photoinitiators are also unsatisfactory because of the tendency to afford polymer casts having an undesirable degree of surface tack or greasiness, this effect generally being known to be due to oxygen inhibition of polymerization at the air/cast surface interface. The initiators useful in accordance with the present invention are (A) 1-hydroxy-1-cyclohexyl phenyl ketone (Irgacure 184, Ciba-Geigy), (B) 2-hydroxy-2,2-dimethyl-acetophenone (Darocure 1173, E. Merck), and a series of aryl ring-substituted derivatives of Darocure 1173 known as Darocure 1116, 1398, 1174, and 1020 [(See Curing by U.V. Radiation (Part 2) J. Ohngemach, et al, Kontakte 3, 15(1980)], and (C) blends of (A) or (B) with azobis (isobutyronitrile).

The formulae of the above mentioned compounds are as follows:

(A) Irgacure 184

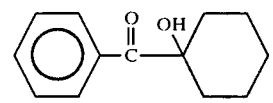

(B) Darocure 1173

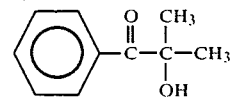

Darocure 1116

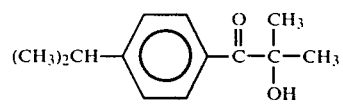

Darocure 1398 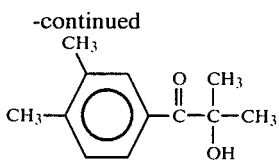

Darocure 1174 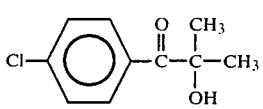

Darocure 1020 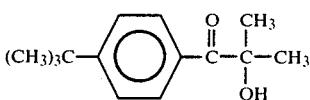

(C) Azobis(isobutyronitrile) 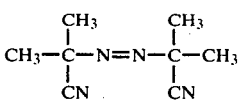

The concentration of the preferred photoinitiators, or blends of two or more photoinitiators, in the formulation can range from about 0.5% to about 20% by weight (preferably 5%–15% by weight) based on the total weight of the (meth)acrylate monomer components. The preferred concentration is dependent on the reactivity of the monomer components, light absorption characteristics of the photoinitiators, and the presence of any other additives in the formulation, such as antioxidants, fillers, and ultraviolet absorbers, which may have an effect on the overall rate of the photochemical reaction. For each monomer formulation, there is generally an optimum photoinitiator concentration range, this being about 5%–10% by weight of the monomers. It has been found that the addition of larger than optimum concentrations can either have no additional beneficial effects or, in many instances, may retard the photopolymerization kinetics and give rise to polymer casts having an undesirable degree of surface tackiness. The optimum concentration is preferably determined experimentally for each monomer/photoinitiator formulation.

Azo catalysts, such as azobis (isobutyronitrile), are also commonly used as photoinitiators. However, when 1%–5% by weight concentrations of the latter were used as the sole photoinitiator, photocuring of the unfilled monomer formulations gave only soft polymer gels. When a blend of 5% of azobis (isobutyronitrile) and about 2% Irgacure 184 or Darocure 1173 was used, the formulation polymerized to a hard, dry, opaque white polymer within one minute exposure to visible light, indicating also a synergistic photoinitiator effect.

Although tertiary organic amines have been commonly used in the past to accelerate the photopolymerization reaction, their use is undesirable in the present invention since they often tend to impart a yellow coloration to the resultant cast.

Surface cure modifiers, such as certain esters of 3-mercaptopropionic acid, constitute a preferred ingredient of the photopolymerizable formulation of the present invention. As disclosed in the Journal of Radiation Curing, April, 1980, pp 10–13, the addition of increasing concentrations of trimethylolpropane tris(3-mercaptopropionate) (TMPTMP) results in a gradual improvement in the surface cure during ultraviolet light-initiated photocuring of certain acrylate urethane oligomer formulations. Dry surface cures result on addition of 5 to 20 (and preferably 5 to 10) parts TMPTMP per 100 parts of ethylenically unsaturated monomer blends. When extended to the visible light cured polymer casts of this invention, excellent surface cures (non-tacky) result from addition of 5 to 10 parts TMPTMP to the formulation. Higher concentrations of TMPTMP are not always beneficial and sometimes result in poorer surface cures. The preferred surface cure modifiers for the compositions of this invention are TMPTMP, pentaerythritol tetrakis(3-mercaptopropionate), and polyethylene glycol di(3-mercaptopropionate) of molecular weight 326–776, the TMPTMP being much preferred.

The TMPTMP surface cure modifier gives improved surface cures for the acrylate-urethane oligomer formulations which are catalyzed with Iragacure 184 and Darocure 1173 photoinitiators. When different photoinitiators are used, such as camphorquinone, poor surface cures and yellow discoloration resulted (See Example 11).

Fiberglass polymer casts, prepared from unfilled monomer formulations, generally have a translucent or glassy apearance, this being due primarily to the transparency or translucency of the glass fabric itself. The opacity of the polymer cast is increased on addition of white fillers to the formulation, this resulting in casts which are more aesthetic in appearance. Suitable fillers are zinc oxide, zinc carbonate, calcium oxide, calcium carbonate, calcium silicate, titanium dioxide, magnesium oxide, natural and synthetic resins, diatomaceous earth, a variety of synthetic silicas, zinc diacrylate, and zinc dimethacrylate. The concentration of filler used in the formulation must be carefully balanced so as not to reduce the visible light transmittance of the composition or rate of photocuring. Concentrations of about 5%–10% by weight of fillers such as zinc diacrylate, zinc dimethacrylate, and the synthetic silicas are effective opacifying agents and do not affect the photocuring rate. It is surmised that the zinc (meth)acrylates may function as reactive fillers which copolymerize with the other monomers present to introduce ionomer type crosslinks.

The monomer formulations may contain antioxidants to improve the shelf-life (decreased dark reaction) of the casting bandages, ultraviolet stabilizers to minimize discoloration in ambient light or sunlight, optical brighteners for whiteness improvement, viscosity modifiers or thixotropic agents to minimize sagging or loss of the photopolymerizable formulation from the cast fabric during storage, and other additives which improve the aesthetic characteristics of the polymer casts without having a deleterious effect on the photocuring reaction.

Experimental casts were prepared by wrapping the wet, tacky, monomer-impregnated fiberglass fabric strips around a 2.75 inch diameter mandril (prewrapped with silicone treated release paper) to give a 5-ply fiberglass cast. The mandril was rotated continuously while exposing the impregnated bandage to visible light for a total of 10 minutes. The cured cast was removed and evaluated for surface tack, color, susceptibility to discoloration in sunlight, and crush strength (pounds of force required to effect a 10 mm diametrial compression of the cast).

The bandaging material of the present invention possesses the following properties:

1. The material is highly permeable to X-rays so that X-ray photographs can be taken through the bandage without any shadow;

2. the bandages required for producing a given supporting effect are much lighter than the known Plaster-of-Paris bandages;

3. the bandages are resistant to water;

4. the bandages may attain weight bearing strength after only 10 minutes;

5. the heat of reaction produced during the hardening of the bandage is slight compared with the conventional Plaster-of-Paris bandages;

6. the cast prepared from the bandages according to the present invention have excellent permeability to air and facilitate moisture evaporation from body surfaces;

7. no eye protection is required for the patient or the applicator, as would be the case when ultraviolet radiation is used.

The present bandage can be applied to the patient immediately. It requires only that the prepared casting substance be unwrapped and bandaged onto the limb. It requires neither a pail of water nor the soaking of prepared plaster-gauze material in water. It has the advantage, too, that no new equipment is required. It is only necessary to expose the wrapped bandage to visible light sources of suitable intensity for a time period of about 10–15 minutes, at the end of which time the bandage will have hardened sufficiently to a weight-bearing strength.

The following examples serve to illustrate the effects of various components of the monomer formulation on the photocure rates, strength properties and overall aesthetics, such as color and resistance to sunlight discoloration of the polymer casts.

EXAMPLE 1

A 2.75 inch diameter mandril was mounted horizontally and connected to a stirring motor. The mandril was covered with a single layer sheet of paper coated with a silicone release agent. A 45 inch strip of fiberglass fabric of 3-inch width was dipped into a photopolymerizable formulation consisting of a blend of 70 parts by weight of an acrylate-terminated polyurethane oligomer (Uvithane 783), 30 parts trimethylolpropane triacrylate (TMPTA), 10 parts trimethylolpropane tris (3-mercaptopropionate) (TMPTMP), and 10 parts 2-hydroxy-2, 2-dimethylacetophenone (Darocure 1173) as photoinitiator. The excess of formulation was removed from the fabric strip to give a resin content of 50% by weight. The impregnated bandage was wound onto the mandril to give a 5-ply wrap. While rotating the bandage continuously, it was exposed to visible light directed from a 150 watt spotlight (General Electric) mounted about 12 inches above the bandage. After a 10 minute exposure to light, the cast was removed and evaluated for color, hardness, crush strength, overall aesthetics, and degree of tackiness or dryness on the outer (air side) and inner (mandril side) surfaces.

The resultant cast was white in color, dry (no tackiness), hard, and showed a crush strength of 45 lbs. The crush strength was the force, in pounds, required to effect a 10 mm diametrical compression of the cured cast when compressed between two platens at a compression rate of 15 inches per minute. The resistance of the cast to discoloration in sunlight was excellent. No yellowing resulted after 5 hours exposure.

EXAMPLE 2

To simulate the protective wrap ordinarily used to protect body members from direct contact with immobilization cast bandages, the apparatus for preparation of the experimental cast in Example 1 was modified by covering the mandril with an ORTHOPLAST stockinette. A 3-inch wide by 45 inch length of fiberglass bandage was impregnated with the formulation of Example 1 to a resin content of 52% by weight and the bandage wrapped on the mandril and cured in the same manner. The polymer cast produced was white, dry to touch on the surface, and showed a crush strength of 32 lbs. No discoloration or yellowing of the cast resulted after 5 hours exposure to sunlight.

The lower, but acceptable, crush strength of the polymer cast as compared to that of Example 1 was a consequence of partial absorption of the incident visible light by the stockinette fabric used as an underwrap. The more reflective white-colored silicone release paper used in Example 1 resulted in a greater degree of internal reflectance of light and higher crush strength of 45 lbs. Still higher strength properties can be achieved using a more highly reflective underwrap, such as a thin layer of aluminum foil.

EXAMPLE 3

Using the method of Example 1 and replacing the 10 parts Darocure 1173 in the formulation with 10 parts of 1-hydroxy-1-cyclohexyl phenyl ketone (Irgacure 184) as photoinitiator, a surface-dry, white, polymer cast showing a crush strength of 40 lbs. at a resins content of 51% by weight was obtained. Exposure of the cured cast to sunlight for 5 hours did not result in any discoloration or yellowing of the cast.

EXAMPLE 4

3" wide×36" length of fiberglass fabric was impregnated with the formulation of Example 3. The impregnated bandage was cut into 6" strips and a six layer laminate prepared. The laminate was placed on the curved surface of the 2.75 inch diameter mandril to simulate the curvature of an orthopedic splint and exposed to visible light from a 150 watt spotlight for 10 minutes. The splint cured to a hard, rigid, non-discolored, and non-tacky (top and bottom surfaces) laminate having a resin content of 49% by weight. No discoloration resulted after a 3 hour exposure of the cured splint to sunlight.

EXAMPLE 5

The formulation of Example 3 was modified by the addition of 5 parts by weight of zinc diacrylate as filler. A fiberglass bandage strip was impregnated with the formulation and a photocured polymer cast prepared in the manner of Example 1. A hard, white, dry to touch, 5-ply copolymer cast showing a crush strength of 46 lbs. at a resins content of 50% by weight was obtained. No discoloration or yellowing of the cast resulted on exposure to bright sunlight for 3 hours.

EXAMPLE 6

The intensity of the visible light source had a significant effect on the rate of photocuring and the strength properties of the cured cast. For example, when a lower intensity and more diffuse 150 watt floodlight was used in place of the 150 watt spotlight of Example 3, 10 minutes photocuring gave a flexible, lower strength polymer cast having a crush strength of only 18 lbs. The surface of the cast was also slightly tacky. When photocured with the more intense 150 watt spotlight for the same time period, higher strength polymer casts of greater than 40 lbs. crush strengths are obtained.

EXAMPLE 7

A glass bandage strip was impregnated with a formulation consisting of 70 parts of an acrylate terminated polyurethane oligomer of relatively high viscosity (Uvithane 893), 30 parts trimethylolpropane triacrylate (TMPTA), 10 parts trimethylolpropane tris(3-mercaptopropionate) (TMPTMP), and 10 parts 1-hydroxy-1-cyclohexyl phenyl ketone (Irgacure 184) to a resins content of 52%. The wet bandage was wound onto the mandril to give a 5-ply cast. The mandril was not rotated. Instead, the wet cast was irradiated for a total of 10 minutes using a hand-held 150 watt spotlight. A dry, non-discolored polymer cast showing a crush strength of 45 lbs. was obtained. No yellowing resulted on exposure of the cured cast to sunlight for one hour, but the crush strength was increased from 45 lbs. to 60 lbs. as a result of postcuring in sunlight. The experiment indicated that greater than 10 minutes exposure to a hand-held 150 watt spotlight was necessary to achieve a fully-cured polymer cast.

EXAMPLE 8

A fiberglass bandage was impregnated with a formulation consisting of 70 parts of an acrylate terminated polyurethane oligomer of relatively high viscosity (Uvithane 893), 30 parts pentaerythritol triacrylate (PETA), 10 parts trimethylolpropane tris(3-mercaptopropionate) (TMPTMP), and 10 parts 1-hydroxy-1-cyclohexyl phenyl ketone (Irgacure 184) and photocured according to the method of Example 1 to give a hard, white, non-tacky polymer cast having a crush strength of 50 lbs. On exposure to sunlight for 3 hours, an insignificant degree of yellowing resulted.

EXAMPLE 9

Using the method of Example 1, visible light curing of a wrapped fiberglass cast impregnated with a formulation consisting of 100 parts of an acrylate terminated polyurethane oligomer of relatively high viscosity (Uvimer 530), 5 parts zinc diacrylate, 10 parts 1-hydroxy-1-cyclohexyl phenyl ketone (Irgacure 184) (no surface cure modifier was used) gave a white, dry-surface polymer cast with a crush strength of 80 lbs.

EXAMPLE 10

To determine the optimum concentration of trimethylolpropane tris(3-mercaptopropionate) (TMPTMP) required as a surface cure modifier, a formulation containing 70 parts of an acrylate terminated polyurethane oligomer of relatively high viscosity (Uvithane 783), 30 parts trimethylolpropane triacrylate (TMPTA), and 20 parts 1-hydroxy-1-cyclohexylphenyl ketone (Irgacure 184) are spiked with 0, 5, and 10 parts of trimethylolpropane tris(3-mercaptopropionate) (TMPTMP). The formulations are transferred to 8 mm deep molds and individually exposed to visible light from a 150 watt spotlight. As shown in the table below, the photocuring reaction is accelerated by addition of increasing amount of TMPTMP, with the optimum surface cures (non-tacky) obtained with use of 5 or 10 parts of TMPTMP in the formulation:

| TMPTMP, Parts by Wt. | Dry surface cure Time, Minutes |
| --- | --- |
| 0 | 8 |
| 5 | 4 |
| 10 | 4 |

EXAMPLE 11

An unfilled monomer blend consisting of 40 parts of an acrylate terminated polyurethane oligomer of relatively high viscosity (Uvithane 783), 60 parts (1,4-butanediol diacrylate (BDDA), 10 parts trimethylolpropane tris(3-mercaptopropionate) (TMPTMP), and 1 part camphorquinone gave hard, tacky, yellow colored polymers on exposure to visible light for 2 minutes. This example shows that camphorquinone when used in the formulations of this invention results in a yellow colored photopolymer not suitable for orthopedic polymer casts.

EXAMPLE 12

Using the general method of Example 1, non-tacky, dry polymer casts (55–58% by weight resin) showing crush strengths of 26–32 lbs. were obtained from a formulation consisting of 60 parts of an acrylate terminated polyurethane oligomer of relatively high viscosity (Uvithane 783), 40 parts tetraethylene glycol diacrylate (TTEGDA), 10 parts trimethylolpropane tris(3-mercaptopropionate) (TMPTMP), and 5 parts 1-hydroxy-1-cyclohexyl phenyl ketone (Irgacure 184).

Replacement of the diluent monomer in the above formulation with a blend of 30 parts TTEGDA and 10 parts trimethylolpropane triacrylate (TMPTA) gave a polymer cast (54% by weight resin) with a highly improved crush strength of 55 lbs. This experiment showed that cast strength properties could be increased by addition of trimethylolpropane triacrylate (TMPTA) and related monomers, such as pentaerythritol triacrylate (PETA) to the formulation. (See Example 8).

EXAMPLE 13

An unfilled formulation consisting of 70 parts of an acrylate terminated polyurethane oligomer of relatively high viscosity (Uvithane 788), 30 parts trimethylolpropane triacrylate (TMPTA), 10 parts trimethylolpropane tris(3-mercaptopropionate) (TMPTMP), and 10 parts 1-hydroxy-1-cyclohexyl phenyl ketone (Irgacure 184) was photocured for 10 minutes with a 150 watt spotlight at 8 inches from the 8 mm deep specimen mold. A dry surface cure resulted after 4 minutes exposure. The polymer specimen was clear, colorless, slightly brittle, and did not yellow to a significant extent on exposure to sunlight for one hour.

Having now described the invention in detail, it should be readily apparent to one skilled in the art that there are various modifications and alterations which may be made without departing from the spirit and scope of the present invention.

I claim:

1. An orthopedic cast material which, when wrapped about a body member and cured by exposure to incandescent visible light which is essentially free of significant actinic radiation in the ultraviolet range of about 200 to 400 nm, forms a rigid, high strength inmobilizing structure and which comprises an air, light and X-ray permeable fabric impregnated with a formulation comprising (a) one or more acrylate terminated polyurethane oligomers, (b) optionally, one or more functional acrylate or methacrylate monomers as reactive diluents and (c) a photoinitiator which is activated by visible light in the wavelength range 400 nm to 750 nm to generate free radicals to initiate the photo polymerization reaction, said photoinitiator being selected from the group consisting of (A) 1-hydroxy-1-cyclohexyl phenyl ketone of the formula

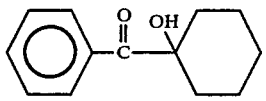

or (B) (ring substituted or unsubstituted) 2-hydroxy 2,2-dimethyl acetophenone of the formula

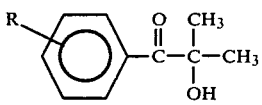

wherein the substituents R are selected from the group consisting of hydrogen, methyl, dimethyl, isopropyl, tertbutyl, chloro, bromo and fluoro, whereby the casts produced therefrom show no tendency towards discoloration in ambient light or sunlight.

2. The material of claim 1, in which the fabric comprises a fiberglass web, the formulation comprising between 40% and 60% by weight of the total weight of the material.

3. The material of claim 1, which includes (d) surface cure modifiers, so that, after curing the resultant cast is non-tacky.

4. The material of claim 3, in which the surface cure modifiers are esters of 3-mercaptopropionic acid.

5. The material of claim 4, in which the surface cure modifiers are selected from the group consisting of trimethylolpropane tris(3-mercaptopropionate), pentaerythritol tetrakis(3-mercaptopropionate) and polyethylene glycol di(3-mercaptopropionate), said surface cure modifiers being present in a range of between 5 and 20 parts per 100 parts of the ethylenically unsaturated monomer.

6. The material of claim 3 in which, after curing, is essentially white in color, and which includes fillers or other opacifying agents to improve cast whiteness and optionally other additives to modify the flow characteristics of the formulation and improve the dark storage stability.

7. The material of claim 1, in which the photoinitiators or blends of two or more photoinitiators comprise from about 0.5% to about 20% by weight, based on the total weight of the (meth)acrylate monomer components.

8. The material of claim 7, in which the photoinitiator comprises from about 5% to about 15% by weight, based on the total weight of the (meth)acrylate monomer components.

9. The material of claim 1 in which the weight ratio of the oligomers (a) to the diluent monomers (b) varies between 40/60 and 100/0.

10. The material of claim 1, in which the weight ratio of the oligomers (a) to the diluent monomers (b) varies between 60/40 and 80/20.

11. The material of claim 6, in which the components of the formulation are present in the following weight ratios: about 70 parts of an aliphatic or aromatic type diacrylate-terminated polyurethane oligomer (a), 30 parts of diluent monomer (b), 10 parts of photoinitiator (c), 10 parts of surface cure modifier and 0–5 parts of an opacifying agent.

12. The material of claim 11, in which (a) is an aliphatic type diacrylate-terminated polyurethane oligomer, (b) is trimethylolpropane triacrylate or pentaerythritol triacrylate, (c) is a photoinitiator of structure (A) or (B), the surface cure modifier is trimethylolpropane tris(3-mercaptopropionate), and the fabric comprises a fiberglass web.

13. The material of claim 6, in which the components of the formulation are present in the following weight ratios: about 100 parts of oligomer (a), zero parts of diluent monomer (b), 10 parts of photoinitiator (c), zero to 10 parts of trimethylolpropane tris(3-mercaptopropionate) as a surface cure modifier and zero to 5 parts of zinc diacrylate as an opacifying agent.

14. The material of claim 1, in which the oligomeric monomer component (a) is prepared from isocyanate terminated prepolymers, wherein the isocyanate moiety of the prepolymer is either aliphatic or aromatic and the reactive diluent monomer (b) is a polyfunctional acrylate or methacrylate ester.

15. The material of claim 6, wherein the filler is zinc diacrylate.

16. A package containing the material of claim 1, comprising an air and light proof aluminum foil sealed bag, or a plastic or metal container.

17. A rigid, high strength inmobilizing cast which is porous, breathable and translucent, comprising the material of claim 1 which has been cured by exposure to incandescent visible light which is essentially free of significant actinic radiation in the ultraviolet range of about 200 to 400 nm.

18. A formulation for use in impregnating a light and X-ray permeable fabric useful for preparing an orthopedic cast material which, when wrapped around a body member and cured by exposure to incandescent visible light which is essentially free of significant actinic radiation in the ultraviolet range of about 200 to 400 nm, forms a rigid, high strength inmobilizing structure, said formulation comprising (a) one or more acrylate terminated polyurethane oligomers, (b) optionally, one or more functional acrylate or methacrylate monomers as reactive diluents, and (c) a photoinitiator which is activated by visible light in the wavelength range 400 nm to 750 nm to generate free radicals to initiate the photopolymerization reaction, said photoinitiator being selected from the group consisting of (A) 1-hydroxy-1-cyclohexyl phenyl ketone of the formula

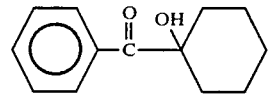

or (B) (ring substituted or unsubstituted) 2-hydroxy-2,2-dimethyl acetophenone of the formula

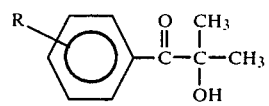

wherein the substituents R are selected from the group consisting of hydrogen, methyl, dimethyl, isopropyl, tert-butyl, chloro, bromo and fluoro.

19. The formulation of claim 18, which includes surface cure modifiers in so that, after curing, the resultant structure is non-tacky.

20. The formulation of claim 19 in which the surface cure modifiers are esters of 3-mercaptopropionic acid.

21. The formulation of claim 20, in which the surface cure modifiers are selected from the group consisting of trimethylolpropane tris(3-mercaptopropionate), pentaerythritol tetrakis(3-mercaptopropionate) and polyethylene glycol di(3-mercaptopropionate), said surface cure modifiers being present in a range of between 5 to 20 parts per 100 parts of ethylenically unsaturated monomer.

22. The formulation of claim 18, which includes fillers or other opacifying agents to improve cast whiteness and, optionally, other additives to modify the flow characteristics of the formulation and improve the dark storage stability.

23. The formulation of claim 18, in which the photoinitiator or blends of two or more photoinitiators (c) comprise from about 0.5% to about 20% by weight, based on the total weight of the (methy)acrylate monomer components [(a) plus (b)].

24. The formulation of claim 18, in which the weight ratio of the oligomers (a) to the monomer diluents (b) varies between 40/60 and 100/0.

25. The formulation of claim 22, in which the components are present in the following weight ratios: about 60 to 70 parts of an aliphatic or aromatic-type diacrylate terminated polyurethane oligomer (a), about 30 to 40 parts of monomer (b), about 10 parts of photoinitiator (c), about 10 parts of surface cure modifier and 0 to 5 parts of an opacifying agent.

26. The formulation of claim 25, in which (a) is an aliphatic type diacrylate-terminated polyurethane oligomer, (b) is trimethylolpropane triacrylate or pentaerythritol triacrylate, (c) is photoinitiator of structure (A) or (B), and the surface cure modifier is trimethylolpropane tris(3-mercaptopropionate).

27. The formulation of claim 22, in which the components are present in the following weight ratios: about 100 parts of oligomer (a), 0 parts of diluent monomer (b), 0 to 10 parts of trimethylolpropane tris(3-mercaptopropionate) as a surface cure modifier, and 0 to 5 parts zinc diacrylate as an opacifying agent.

28. The formulation of claim 22, in which the filler is zinc diacrylate.

29. A method of forming an orthopedic cast, which comprises wrapping a body member with the material of claim 1, and curing and hardening the latter by exposing same to incandescent visible light in the wavelength range of 400 nm to 750 nm for at least two minutes, said visible light being essentially free of significant actinic radiation in the ultraviolet range of about 200 to 400 nm.

30. The material of claim 1 wherein photoinitiator (A) is additionally blended with azobis(isobutyronitrile).

31. The material of claim 1 in which photoinitiator (B) is additionally blended with azobis(isobutyronitrile).

32. The formulation of claim 18 in which photoinitiator (A) is additionally blended with azobis(isobutyronitrile).

33. The formulation of claim 18 in which photoinitiator (B) is additionally blended with azobis(isobutyronitrile).

* * * * *

UNITED STATES PATENT AND TRADEMARK OFFICE
CERTIFICATE OF CORRECTION

PATENT NO. : 4,512,340

DATED : April 23, 1985

INVENTOR(S) : Carl J. Buck

It is certified that error appears in the above-identified patent and that said Letters Patent is hereby corrected as shown below:

Column 17, line 26, "(methy)acrylate" should read -- (meth)acrylate --.

Signed and Sealed this

Eighth Day of July 1986

[SEAL]

Attest:

DONALD J. QUIGG

Attesting Officer     Commissioner of Patents and Trademarks

UNITED STATES PATENT AND TRADEMARK OFFICE
CERTIFICATE OF CORRECTION

PATENT NO. : 4,512,340
DATED : April 23, 1985
INVENTOR(S) : Carl J. Buck

It is certified that error appears in the above-identified patent and that said Letters Patent is hereby corrected as shown below:

Claim 6, line 43 delete "claim 3 in which" and insert
-- claim 3 which --.

Claim 17, line 29 delete "inmobilizing" and insert
-- immobilizing --.

Claim 18, line 42 delete "inmobilizing" and insert
-- immobilizing --.

Claim 19, line 5 delete "is so that" and insert -- so that --.

Signed and Sealed this

Twelfth Day of August 1986

[SEAL]

Attest:

DONALD J. QUIGG

Attesting Officer

Commissioner of Patents and Trademarks